(12) United States Patent
Axon et al.

(10) Patent No.: US 6,293,907 B1
(45) Date of Patent: Sep. 25, 2001

(54) ENDOSCOPE COVER HAVING PROTRUSIONS

(76) Inventors: Anthony Thomas Roger Axon, Upwood, Woodlands Drive, Rawdon, Leeds LS19 6JZ (GB); Patrick Robert Axon, 1 Westgate, Hale, Altringham WA15 9AY (GB); Andrew Eliot Axon, 95 The Avenue, Harewood, Leeds LS17 9LD (GB)

( * ) Notice: Subject to any disclaimer, the term of this patent is extended or adjusted under 35 U.S.C. 154(b) by 0 days.

(21) Appl. No.: 09/194,094
(22) PCT Filed: May 23, 1997
(86) PCT No.: PCT/GB97/01424
  § 371 Date: Nov. 20, 1998
  § 102(e) Date: Nov. 20, 1998
(87) PCT Pub. No.: WO97/43941
  PCT Pub. Date: Nov. 27, 1997

(30) Foreign Application Priority Data

May 23, 1996 (GB) .................................................. 9610765

(51) Int. Cl.[7] ....................................................... A61B 1/00
(52) U.S. Cl. ........................... 600/114; 600/121; 600/124
(58) Field of Search .................................... 600/114, 115, 600/116, 121, 124, 125; 604/95

(56) References Cited

U.S. PATENT DOCUMENTS

| 3,635,223 | * | 1/1972 | Klieman ................................ 606/194 |
| 3,665,928 | * | 5/1972 | Del Guercio ........................... 604/95 |
| 3,871,358 | * | 3/1975 | Fukuda et al. ........................ 600/114 |
| 3,913,565 | * | 10/1975 | Kawahara ............................. 600/585 |
| 4,207,872 | * | 6/1980 | Meiri et al. .......................... 600/116 |
| 5,454,364 | * | 10/1995 | Kruger ................................. 600/114 |
| 5,591,202 | * | 1/1997 | Slater et al. ......................... 600/205 |
| 5,595,565 | * | 1/1997 | Treat et al. .......................... 600/114 |
| 5,707,342 | * | 1/1998 | Tanaka ................................. 600/114 |

* cited by examiner

Primary Examiner—John P. Leubecker
(74) Attorney, Agent, or Firm—Sidley & Austin; Hugh A. Abrams

(57) ABSTRACT

A removable cover of an endoscope shaft (2) includes a sleeve (4) of elastic material having a low friction external surface configured so that the frictional resistance to forward displacement of the endoscope shaft is less than the frictional resistance to reverse movement of the endoscope shaft.

15 Claims, 2 Drawing Sheets

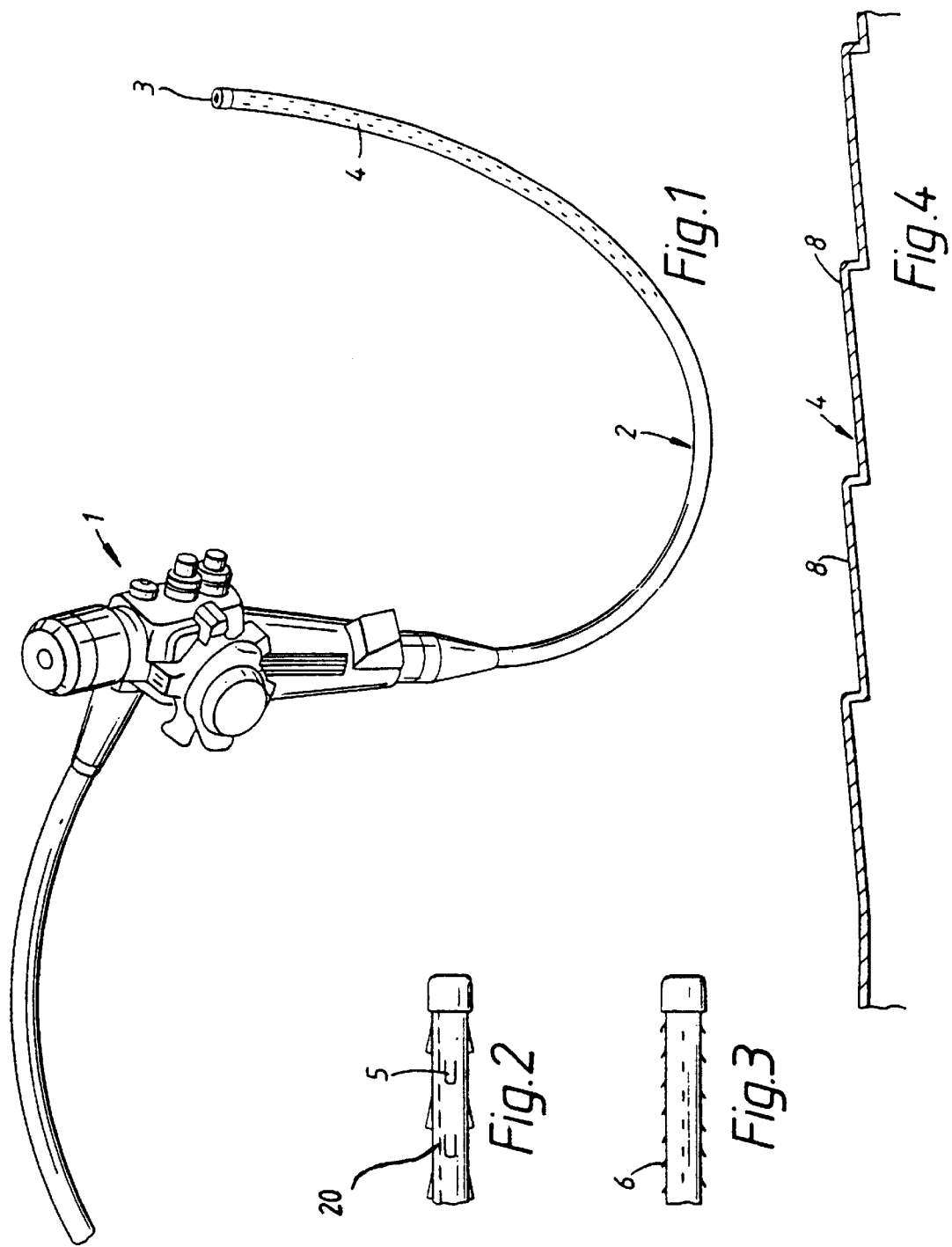

ENDOSCOPE COVER HAVING PROTRUSIONS

BACKGROUND OF THE INVENTION

The present invention relates to endoscopes and to covers or sleeves for endoscopes.

Flexible endoscopic equipment has been used in medicine since the late 1960's; however, the basic design of the equipment has not changed significantly since the early 70's. Its main use is in the diagnosis and treatment of gastrointestinal disorders because internal organs can be directly visualised, abnormalities targeted and specimens removed for microscopic analysis. Endoscopy has also become important in treating patients because surgical instruments can be introduced through the endoscope. Small tumors can be removed, laser therapy performed, injections given, narrowed areas can be stretched and foreign bodies removed. Early endoscopes included fibre optics for viewing purposes, but more modern endoscopes operate on video imaging principles using an electronic chip with the image being displayed on a television screen.

There are four main types of endoscope used in gastroenterology: an upper digestive endoscope passed through the mouth for examination of the gullet, stomach and the duodenum; a duodenoscope for pancreatico-bilary work; a colonoscope for inspection of the large intestine (colonoscopy); and an enteroscope for inspection of the small intestine (enteroscopy).

In order to perform colonoscopy patients first undergo a stringent laxative regimen in order to clear the large intestine of fecal matter. They are given a light sedative and an analgesic and the flexible endoscopic instrument is introduced through the anus and passed up through the large intestine. The limit of the examination is usually the caecum which is the upper most part of the large bowel but skilled operators can introduce the instrument into the lower part of the small intestine.

The performance of colonoscopy is technically difficult and requires a long period of learning. Even after training, some operators are more skillful than others and are able to perform the procedure more quickly, safely and effectively than others. The reason why the procedure can be difficult is that the colon is variable in its shape and configuration. It comprises a series of loops which are tethered within the abdomen in certain places by the blood vessels and connective tissue which supply the organ whereas in other parts, the colon is relatively free to move around within the abdominal cavity. When a flexible, but fairly stiff instrument is inserted into the bowel there is a tendency for looping to occur. When this happens the skilled operator is able to reduce the size of the loop and concertina the bowel over the instrument. By twisting, pushing, pulling and angling of the tip of the instrument progress is made around the bowel until the caecum is reached. Less skilled endoscopists find this difficult and often large loops are formed within the abdomen. When this occurs not only is further progress difficult, but it is painful for the patient and there are potential risks that the mesentry may be pulled excessively. The length of time to reach the caecum varies from 10 minutes to over one hour and, on occasions it is not possible to reach the caecum at all.

Colonoscopy is the most effective technique available for examining the large intestine. Not only has it been advocated as a diagnostic test for patients with colonic symptoms and diseases it is also used for cancer screening. (Colonic cancer in the United Kingdom is the second commonest lethal cancer.) The particular relevance of colonoscopy is that these cancers usually begin as small polyps which can be easily removed by the colonoscope before they become malignant and it would be possible to reduce the risk of cancer very substantially if colonoscopy was easy and simple. However, its popularity as a screening technique is limited by expense of the procedure and the unpleasantness to the patient. If it were possible to reach the caecum regularly within a short period of time and without discomfort the technique would be more widely applicable.

It has been estimated recently that in the United Kingdom alone as many as 250,000 colonoscopic examinations are performed per annum. If it was more acceptable and cheaper the number would be considerably in excess of this. The main expense relates to staffing and overheads rather than capital equipment, thus if more patients could be examined per unit time the costs would fall considerably.

Enteroscopy is not a commonly used procedure, one main reason for which is its difficulty. The small intestine is the longest part of the gastrointestinal tract and it can be reached only by passing the endoscope first through the gullet, stomach and duodenum; only then is the small intestine entered. The small intestine itself is convoluted with many twists and turns and attempts to advance the enteroscope through the small intestine is difficult, painful and enables only the upper part of the small intestine to be examined. The reason for this is that when using a "push" enteroscope the bends that occur in the enteroscope prevent it from advancing with the result that it tends to coil up and looping occurs. Another way of doing enteroscopy is to use a "pull" enteroscope which is much thinner and is passed through the nose and then allowed to travel (as food does) under its own momentum through the small intestine. It can be withdrawn and the small intestine can be viewed as it comes out. Unfortunately it tends to slip rapidly around, twisting and turning and the whole intestine still cannot be easily seen. Furthermore because it is so thin it is not possible to carry out treatment procedures through it.

SUMMARY OF THE INVENTION

It is an object of a preferred embodiment of the invention to provide an endoscope with an external surface which permits digestive endoscopy including colonoscopy and enteroscopy to be accomplished more quickly, safely and with less discomfort that is possible with current equipment.

According to one broad aspect the present invention resides in a cover for an endoscope shaft, comprising a sleeve having a low friction surface in at least the direction of forward displacement to facilitate the use of the endoscope shaft.

The invention also resides in an endoscope comprising a flexible shaft with a proximal end for connection to a viewing means, and a free distal end, wherein over at least part of its length the shaft has a surface arranged to provide less frictional resistance to forward displacement of the shaft through a body passage, into which the shaft is inserted in use, than to reverse displacement of the shaft through the body passage.

The endoscope can be provided with low friction surface, which may take the form of a special surface coating, advantageously of a low friction polymer. One form is a coating of silicone fluid which is applied wet and then allowed to dry to produce a very thin low friction coating. Also, the low friction surface may be provided by the covering sleeve, the surface of which can be configured to ensure the differential friction as between forward and reverse displacement through a body passage, e.g. the bowel, into which it is inserted. The sleeve will extend over at least part of the length of the endoscope shaft from the distal end and preferably extends over all or most of its length. The sleeve is advantageously thin walled, e.g. less than 0.5 mm, such as 0.1 mm to 0.3 mm and sufficiently elastic to grip the flexible shaft. It is not essential for the sleeve to exert a tight grip on the endoscope shaft and for ease of application of the sleeve to the shaft a light grip is preferable. The friction between the sleeve and shaft can prevent their relative displacement longitudinally without requiring the sleeve to grip the endoscope shaft. Furthermore, it may be desirable, particularly if the sleeve is formed of material having a fairly high coefficient of friction and/or has a close fit around the shaft, to provide a coating on the inner surface of the sleeve to reduce friction and hence assist application of the sleeve to the endoscope shaft, and possibly subsequent removal of the sleeve from the shaft. If the sleeve is produced by moulding on a mandrel or former, the internal coating can be applied over the sleeve material with the sleeve subsequently being removed from the mandrel and turned inside out, this technique being known for the manufacture of other articles such as surgical gloves.

As far as the external frictional properties of the sleeve are concerned, reliance could be placed on the low friction characteristics of the material of the sleeve itself or a low friction coating possibly of the type described above could be applied to the external surface of the sleeve. Conveniently the sleeve can be dip moulded on a mandrel, and suitable elastic materials include natural rubber, polychloroprene, and polyurethane. The external surface of the sleeve can be treated to modify, in particular reduce, the surface friction. A very lubricious surface can be obtained by use of a hydrophilic hydrogel polymer. If desired a lubricant can be applied to the exterior of the sleeve. The frictional resistance differs in the forward and reverse directions, which correspond in use to the insertion and withdrawal direction. With the frictional resistance being less in the forward direction than in the reverse direction, the endoscope can selectively pull the bowel when a withdrawing force is applied to the endoscope shaft, which in turn facilitates the reduction in loops in the bowel by causing the bowel to concertina itself on the endoscope. The difference in friction can be achieved by surface protrusions or texturing either over a part or the whole length of the flexible shaft. Texturing can be formed by an outer coating, but most conveniently the sleeve is formed with protrusions similar to fishscales or with shallow wedge shapes. Alternatively, backward facing bristles, for example, arranged in rings spaced along the sleeve, may be employed. In a further alternative a propulsive mechanism such as a worm or snake or air insulation or water injection in a pulsed manner could be employed.

It should be understood that although greater resistance to reverse movement of the endoscope shaft is provided it will still be possible to withdraw the endoscope without trauma to the bowel and, in the case of a colonoscope, in particular to the anal mucosa which normally grips the outside of the endoscope tightly. For ease of withdrawal the sleeve can be adapted to facilitate separate removal of the sleeve and endoscope shaft, for which purpose the sleeve may be provided with a longitudinal line of weakness 20 (as shown in FIG. 2) along which it can be torn to facilitate separation of the shaft and sleeve.

BRIEF DESCRIPTION OF THE DRAWINGS

In order that the invention may be more clearly understood, embodiments of the invention will now be described by way of example with reference to the accompanying drawings in which:

FIG. 1 shows diagrammatically an endoscope according to the invention;

FIG. 2 shows to a larger scale a part of the endoscope of FIG. 1;

FIG. 3 is a view similar to FIG. 2 and shows a modified form of sleeve;

FIG. 4 is a longitudinal cross section through a side wall of an alternative form of sleeve.

DETAILED DESCRIPTION OF THE PREFERRED EMBODIMENTS

Figure 5:
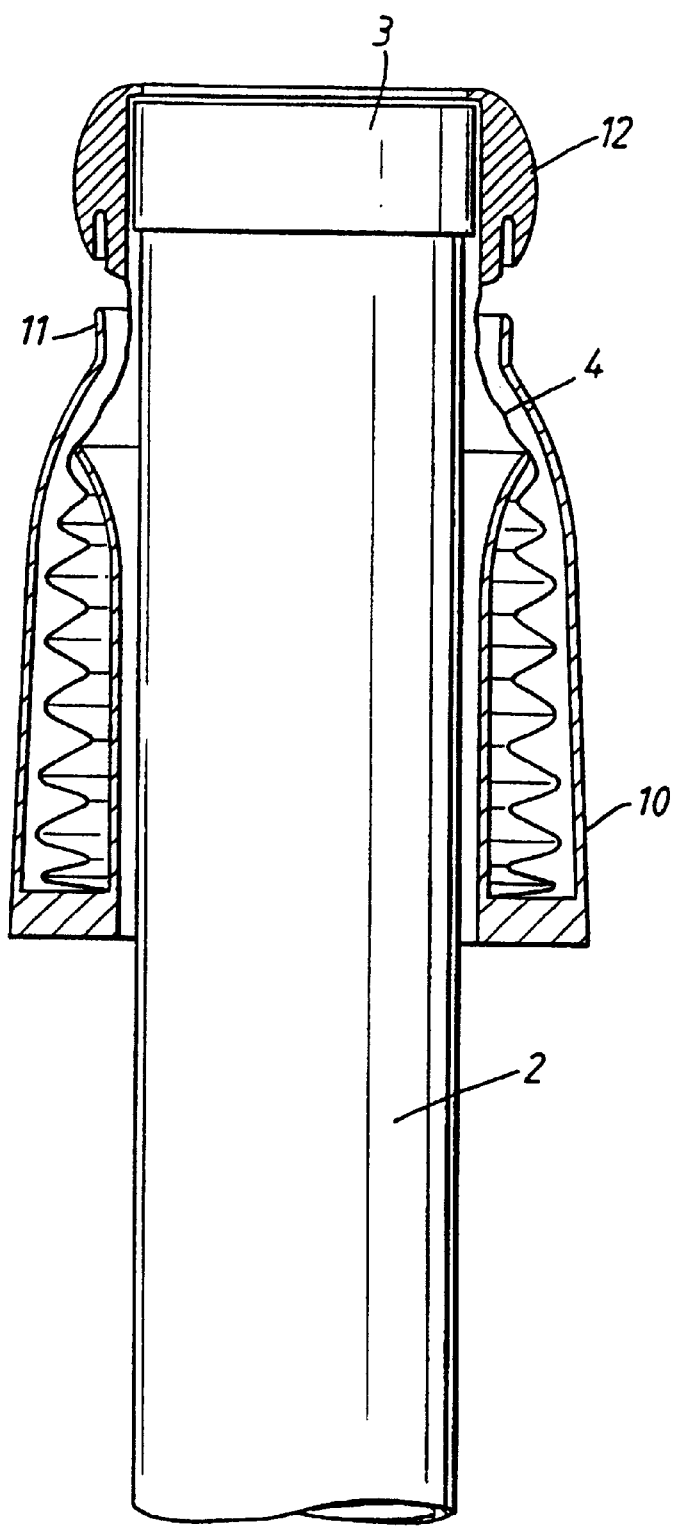
FIG. 5 is a schematic illustration of an applicator for use in applying the sleeve to an endoscope shaft.

Referring to FIG. 1, the endoscope is basically of conventional construction and comprises an eyepiece section 1 and an insertion shaft 2. The distal end 3 of the insertion shaft 2 comprises lenses, channels and light guides. Of course the endoscope could instead be adapted for video imaging as is well known in the art. A sleeve 4 is applied over the insertion shaft 2 and extends over the whole or a part of its length.

The sleeve may be either disposable or sterilisable, and if disposable may be available in a sterile pack. It is of robust manufacture, so that it will not break or become worn during usage and is made of electrically insulating material and sufficiently flexible not to interfere with the action of the endoscope itself. It is suitable for use in a wet dirty environment and is of a suitable size for use with a wide range of manufacturers' instruments. Accordingly the sleeve is constructed of non toxic material which has a low coefficient of friction and should be flexible, robust, either disposable or suitable for sterilisation. This sleeve is inherently capable of attaching to the endoscope, does not conduct electricity and is water resistant (non wettable). The sleeve is made of material sufficiently elastic for the sleeve to grip the shaft of the endoscope so that the sleeve does not slip along the shaft in use of the endoscope.

The sleeve is "user friendly" so that it is easy and quick to fit to the instrument, easy to remove and as simple as possible. The operator may then retain complete control over the manipulation of the instrument during use. It should be of a "clinical" appearance.

Referring particularly to FIG. 2, the external surface of the sleeve 4 is configured with protrusions to produce a "fishscale" finish 5. This produces a surface which has a lower coefficient of friction in the forward/insertion direction than in the reverse/withdrawal direction. For ease of withdrawal the sleeve can be adapted to facilitate separate removal of the sleeve and endoscope shaft, for which purpose the sleeve may be provided with a longitudinal line of weakness along which it can be torn to facilitate separation of the shaft and sleeve. FIG. 3 shows an alternative arrangement of FIG. 2 in which fine hairs or bristles 6 are provided to provide the above mentioned differential coefficient of friction. The length, stiffness, thickness, variation of thickness along their length, pliability and nature of the ends of the scale or bristles may be varied as desired. These may be continuous or spaced out.

An alternative sleeve construction is shown in FIG. 4 and is particularly suited to manufacture of the sleeve by moulding on a mandrel, for example by a dip moulding process. The sleeve 4 is formed with protrusions 8 of wedge shape profile continuously along the sleeve so that a saw-tooth profile is obtained. The wedge-shape protrusions could be annular and extend continuously around the sleeve circumference. Alternatively they may be discrete and spaced apart. The wedges are inclined at a shallow angle, for example 5° to 10° to the sleeve axis, and the inclined faces can be of any appropriate length, for example 5 mm to 10 mm. The rear or trailing faces of the wedge shaped protrusions are preferably substantially perpendicular to the sleeve axis.

FIG. 5 illustrates an endoscope cover during application to an endoscope shaft. The sleeve of the cover is concertina folded into an annular holder 10 having an opening at one end through which the forward end of the sleeve 4 protrudes. The outer wall of the holder is extended to form a guide collar 11 to assist in guiding the sleeve onto the endoscope shaft 2. The sleeve in this embodiment is provided with a ring 12 at its forward end, this ring being adapted to engage over the distal end 3 of the endoscope shaft. The holder 10 is passed over the end of the shaft 2 to bring the ring into engagement with the distal end 3, and the holder is displaced along the shaft, which moves through the holder with a clearance, so that the sleeve is progressively dispensed from the holder and covers the shaft 2 which it grips due to the inherent resilience of the sleeve material.

It will be appreciated that the above embodiments have been described by way of example only and that many variations are possible without departing from the scope of the invention. The sleeve may be designed to be inflated, such that the propulsive mechanism is operative only in the inflated (or deflated) state, enabling withdrawal to be accomplished with greater safety.

What is claimed is:

1. A removable cover for an endoscope shaft, the cover comprising an elongate sleeve (4) of thin elastic material, the sleeve having a single tubular wall with an inner surface and an outer surface, the sleeve being arranged for application over an endoscope shaft (2) with the sleeve extending along at least a major part of the length of the shaft and with close contact between the inner surface and the shaft holding the sleeve against movement longitudinally of the shaft during displacement of the shaft through a body passage into which the shaft is inserted in use, and the outer surface of the sleeve has protrusions so configured that the cover and the endoscope shaft onto which the cover is applied have a low frictional resistance during forward displacement of the endoscope shaft and cover through the body passage and a greater frictional resistance during rearward displacement of the endoscope shaft and cover through the body passage, wherein the sleeve has protrusions of wedge-shaped profile in longitudinal section.

2. A removable cover for an endoscope shaft, the cover comprising an elongate sleeve (4) of thin elastic material, the sleeve having a single tubular wall with an inner surface and an outer surface, the sleeve being arranged for application over an endoscope shaft (2) with the sleeve extending along at least a major part of the length of the shaft and with close contact between the inner surface and the shaft holding the sleeve against movement longitudinally of the shaft during displacement of the shaft through a body passage into which the shaft is inserted in use, and the outer surface of the sleeve has protrusions so configured that the cover and the endoscope shaft onto which the cover is applied have a low frictional resistance during forward displacement of the endoscope shaft and cover through the body passage and a greater frictional resistance during rearward displacement of the endoscope shaft and cover through the body passage, wherein the sleeve (4) has a line of weakness extending therealong to facilitate lengthwise tearing of the sleeve for removal of the sleeve from the endoscope.

3. A removable cover for an endoscope shaft, the cover comprising an elongate sleeve (4) of thin elastic material, the sleeve having a single tubular wall with an inner surface and an outer surface, the sleeve being arranged for application over an endoscope shaft (2) with the sleeve extending along at least a major part of the length of the shaft and with close contact between the inner surface and the shaft holding the sleeve against movement longitudinally of the shaft during displacement of the shaft through a body passage into which the shaft is inserted in use, and the outer surface of the sleeve has protrusions so configured that the cover and the endoscope shaft onto which the cover is applied have a low frictional resistance during forward displacement of the endoscope shaft and cover through the body passage and a greater frictional resistance during rearward displacement of the endoscope shaft and cover through the body passage, wherein the sleeve is accommodated in an annular housing (10) having a central aperture through which the endoscope shaft (2) is movable during application of the sleeve to the shaft.

4. An endoscope comprising an elongate flexible shaft (2) having a proximal end connected to viewing means (1) and a free distal end (3), with an outer layer of material covering the shaft over at least a major part of its length, the shaft having a substantially constant diameter along at least the length thereof covered by the outer layer, the outer layer of material being firmly supported on the inside thereof, said outer layer defining an exterior surface having protrusions thereon configured to provide less frictional resistance to forward movement of the shaft than to reverse movement of the shaft.

5. An endoscope as claimed in claim 4, wherein the outer layer is defined by a removable sleeve which extends over at least a major part of the length of the elongated shaft from the distal end thereof.

6. Am endoscope according to claim 5, wherein the sleeve (4) is made from elastic material, selected from the group consisting of polyurethane, polychloroprene or natural rubber.

7. An endoscope according to claim ,5 wherein the external surface has a coating of lower frictional characteristics than the material of the sleeve.

8. An endoscope according to claim 7, wherein the external surface has a coating of lower frictional characteristics than the material of the sleeve.

9. An endoscope according to claim 7, wherein the external surface has a lubricant applied thereto.

10. An endoscope as claimed in claim 4, wherein the protrusions defined at the exterior surface are inclined at a shallow angle.

11. An endoscope as claimed in claim 10, wherein the protrusions have the form of fish scales (5), that is generally flat elements hingedly connected to the outer layer at the forward edges.

12. An endoscope as claimed in claim 10, wherein the protrusions (8) are wedge-shaped.

13. An endoscope as claimed in claim 10, wherein the protrusions comprise bristles (6).

14. An endoscope as claimed in claim 4, wherein the outer layer is defined by a cover which is selectively adjustable to facilitate removal of the shaft from the body passage.

15. An endoscope as claimed in claim 4, wherein the outer layer is defined by a sleeve having a line of weakness to facilitate separation of the sleeve from the elongated shaft and allow separate withdrawal of the sleeve and flexible shaft from the body passage.

* * * * *